(12) United States Patent
Trant

(10) Patent No.: US 6,989,164 B2
(45) Date of Patent: Jan. 24, 2006

(54) METHOD AND COMPOSITION FOR IMPROVING MALE FERTILITY HEALTH

(75) Inventor: Aileen Sontag Trant, Mountain View, CA (US)

(73) Assignee: The Daily Wellness Company, Mountain View, CA (US)

( * ) Notice: Subject to any disclaimer, the term of this patent is extended or adjusted under 35 U.S.C. 154(b) by 324 days.

(21) Appl. No.: 10/117,169

(22) Filed: Apr. 8, 2002

(65) Prior Publication Data

US 2002/0142052 A1 Oct. 3, 2002

Related U.S. Application Data

(63) Continuation-in-part of application No. 09/742,412, filed on Dec. 22, 2000, now Pat. No. 6,497,885.

(51) Int. Cl.
*A61K 35/78* (2006.01)

(52) U.S. Cl. ............... 424/729; 424/725; 424/702; 424/641; 514/52; 514/458; 514/474

(58) Field of Classification Search ............... 424/729, 424/725, 702, 641; 514/52, 458, 474
See application file for complete search history.

(56) References Cited

U.S. PATENT DOCUMENTS

| | | | |
|---|---|---|---|
| 2,878,124 A | 3/1959 | Kruckenberg |
| 3,015,567 A | 1/1962 | Hause et al. |
| 3,360,374 A | 12/1967 | Barr et al. |
| 3,970,750 A | 7/1976 | Brockemeyer et al. |
| 4,154,813 A | 5/1979 | Kleinberg |
| 4,168,307 A | 9/1979 | Okamoto et al. |
| 4,340,592 A | 7/1982 | Adibi |
| 4,388,325 A | 6/1983 | Orzalesi |
| 4,599,232 A | 7/1986 | Bertelli |
| 4,753,926 A | * | 6/1988 | Lucas et al. |
| 4,774,089 A | * | 9/1988 | Ashmead |
| 4,900,566 A | 2/1990 | Howard |
| 4,920,098 A | 4/1990 | Cotter et al. |
| 4,945,115 A | * | 7/1990 | Liu |
| 4,954,526 A | 9/1990 | Keefer |
| 4,957,938 A | 9/1990 | Anderson et al. |
| 5,032,608 A | 7/1991 | Dudrick |
| 5,034,377 A | 7/1991 | Adibi et al. |
| 5,036,052 A | 7/1991 | Ozeki et al. |
| 5,041,429 A | 8/1991 | Sawai et al. |
| 5,106,836 A | 4/1992 | Clemens et al. |
| 5,157,022 A | 10/1992 | Barbul |
| 5,171,217 A | 12/1992 | March et al. |
| 5,217,997 A | 6/1993 | Levere et al. |
| 5,221,668 A | 6/1993 | Henningfield et al. |
| 5,248,688 A | 9/1993 | Dudrick |
| 5,262,435 A | 11/1993 | Joshua et al. |
| 5,278,189 A | 1/1994 | Rath et al. |
| 5,288,490 A | 2/1994 | Budzynski et al. |
| 5,292,538 A | * | 3/1994 | Paul et al. |
| 5,296,246 A | 3/1994 | Inoue et al. |
| 5,326,569 A | 7/1994 | Acosta et al. |
| 5,334,617 A | 8/1994 | Ulrich et al. |
| 5,364,644 A | 11/1994 | Walaszek et al. |
| 5,374,651 A | 12/1994 | Kilbourn et al. |
| 5,380,945 A | 1/1995 | Murad et al. |
| 5,385,937 A | 1/1995 | Stamler et al. |
| 5,385,940 A | 1/1995 | Moskowitz |
| 5,411,956 A | 5/1995 | Miyazaki et al. |
| 5,428,070 A | 6/1995 | Cooke et al. |
| 5,439,938 A | 8/1995 | Snyder et al. |
| 5,464,644 A | 11/1995 | Wullschleger et al. |
| 5,500,266 A | 3/1996 | Durnin |
| 5,523,087 A | 6/1996 | Shlyankevich |
| 5,543,430 A | 8/1996 | Kaesemeyer |
| 5,545,414 A | * | 8/1996 | Behr et al. |
| 5,576,287 A | 11/1996 | Zaloga et al. |
| 5,576,351 A | 11/1996 | Yoshimura et al. |
| 5,594,032 A | 1/1997 | Gonzalez-Cadavid et al. |
| 5,626,883 A | 5/1997 | Paul |
| 5,631,031 A | 5/1997 | Meade |
| 5,650,418 A | 7/1997 | Rath et al. |
| 5,730,987 A | 3/1998 | Omar |
| 5,767,160 A | 6/1998 | Kaesemeyer |

(Continued)

FOREIGN PATENT DOCUMENTS

| | | |
|---|---|---|
| EP | 441119 | 8/1991 |
| EP | 511587 | 4/1992 |
| EP | 511118 | 10/1992 |
| EP | 0546796 | 6/1993 |
| JP | 50 48189 | 4/1975 |
| JP | 57 5692 | 1/1982 |
| JP | 57 93913 | 6/1982 |
| JP | 58-55418 | 4/1983 |
| JP | 05-163139 | 6/1993 |
| JP | 06-321786 | 11/1994 |
| JP | 07 163269 | 6/1995 |
| WO | WO93 18156 | 9/1993 |
| WO | WO94/01006 | 1/1994 |
| ZA | 94 10015 | 9/1993 |

OTHER PUBLICATIONS

Scott et al. British Journal of Urology (1998), vol. 82, pp. 76–80.*

(Continued)

*Primary Examiner*—Susan D. Coe
(74) *Attorney, Agent, or Firm*—James Creighton Wray; Meera P. Narasimhan

(57) ABSTRACT

L-carnitine, an amino acid, improves sperm quality and motility. Ferulic acid, an antioxidant found in Dong quai, also improves sperm quality. Sperm are highly susceptible to free radical or oxidative damage from environmental toxicants and natural aging. Vitamins C and E, green tea, and selenium are all potent antioxidants that help improve overall reproductive health. Zinc and B vitamins (B6, B 12 and folate) are critical nutrients in male reproductive systems for hormone metabolism, sperm formation and motility.

7 Claims, No Drawings

U.S. PATENT DOCUMENTS

| | | | |
|---|---|---|---|
| 5,780,039 A | | 7/1998 | Greenberg et al. |
| 5,788,971 A | * | 8/1998 | Togasaki |
| 5,852,058 A | | 12/1998 | Cooke et al. |
| 5,861,168 A | | 1/1999 | Cooke et al. |
| 5,883,086 A | * | 3/1999 | Craft |
| 5,891,459 A | | 4/1999 | Cooke et al. |
| 5,895,652 A | * | 4/1999 | Giampapa |
| 5,897,864 A | | 4/1999 | Cohen |
| 5,910,308 A | * | 6/1999 | D'Jang |
| 5,945,452 A | | 8/1999 | Cooke et al. |
| 5,948,443 A | * | 9/1999 | Riley et al. |
| 5,976,568 A | * | 11/1999 | Riley |
| 6,007,824 A | | 12/1999 | Duckett et al. |
| 6,117,872 A | | 9/2000 | Maxwell et al. |
| 6,261,607 B1 | * | 7/2001 | Newmark et al. |

OTHER PUBLICATIONS

Zheng et al. Free Radical Biology and Medicine (1997), vol. 22, No. 4, pp. 581–586.*

Balch et al. Prescription for Nutritional Healing (1997), pp. 338–339.*

Costa et al. Andrologia (1994), vol. 26, pp. 155–159.*

Dawson et al. Fertility and Sterility (1992), vol. 58, No. 5, pp. 1034–1039.*

Derwent English abstract of German Pat. Appl. No. 3931693 A (Apr. 1991).*

Paick et al.; *An experimental study of the effect of ginkgo biloba extract on the human and rabbit corpus cavernosum tissue;* The Journal of Urology, vol. 156, Nov. 1996; pp. 1876–1880.

Internet Search Results, WebMD Health; Search Topics: "amino" amino acid; Branched–chain Amino Acids; Non-essential Amino Acids; Ginkgo; Ginseng; Protein in Diet; Want a Love Potion?; http://my.webmd.com; Jul. 23, 2001; 19 pages.

Internet Search Results, Auravita Health Channel; Search Topics: *Arginine: Asian Ginseng: Dehydroepiandrosterone(DHEA): Ginkgo biloba: Impotence:* www.auravita.com; Jul. 23, 2001; 17 pages.

Kaplan et al.; *Safety and efficacy of sildenafil in postmenopausal women with sexual dysfunction;;* Urology, vol. 53, 1999; pp. 481–486.

Article Query, Pubmed medline; *Berman et al.; Effect of Estrogen withdrawal . . . (Urology, 1988); Goldstein et al., Vasulogenic female sexual dysfunction, (IntJImpotRes. 1998); Rosen et al., Effect of SSRIs on sexual function(JClin Psychphar. 1999); Pau et al., Dietary arginine . . . (JNutr. 1982)* (Abstracts).

McLeod, David; *Female Infertility: a holistic approach;* Australian Journal of Medicine Herbalism, vol. 8, No. 3; pp. 68–77.

Propping et al.; *Diagnostik und Therapie der Gelbkorperschwache in der Praxis;* Therapiewoche; vol. 38, No. 41 (1998); pp. 2993–3001.

Moriyama et al.; *Studies on the usefulness of a long–term, high–dose treatment of methycobalamin for patients with oligozoospermia;* (In Japanese except for Abstract); 1987; pp. 151–156.

Netter et al.; *Effect of Zinc Administration on Plasma Testosterone. Dihydrotestosterone, and Sperm Count;* Archives of Andrology, vol. 7, (1981); pp. 69–73.

Czeizel, Andrew E.; *Periconceptional folic acid containing multivitamin supplementation;* European Journal of Obstetrics & Gynecology and Reproductive Biology; Vil. 78 (1998); pp. 151–161.

Takihara et al.; *Zinc sulfate therapy for infertile male with or without variococelectomy;* Urology, vol. XXIX, No. 6; Jun. 1987; pp. 638–641.

Hishikawa et al.; *Effect of Systemic L–Arginine Administration on Hemodynamics and Nitric Oxide Release in Man;* Japanese Heart Journal, Jan. 1992; pp. 41–48.

Brown, Donald J. *Vitex agnus castus Clinical Monograph,* Townsend Letter for Doctors and Patients, Oct. 1995, pp. 138–142.

Various, *Study Abstracts and Results re Vitex,* Phytotherapy Research Compendium, pp. 23 and 24, 1994.

Caan et al.; *Differences in Fertility Associated with Caffeinated Beverage Consumption,* American Journal of Public Health, vol. 88, No. 2, Feb., 1998: pp. 270–274.

Kessopoulou et al., *A double–blind randomized placebo cross–over controlled trial using the antioxidant vitamin E to treat reactive oxygen species associated male infertility,* Fertility and Sterility, vol. 64, No. 4, Oct. 1995: pp. 825–831.

Bayer, *Treatment of Infertility with Vitamin E,* International Journal of Fertility, vol. 5, No. 1, Jan.–Mar. 1960: pp. 70–78.

Geva et al., *The effect of antioxidant treatment on human spermatazoa and fertilization rate in an in vitro fertilization program,* Fertility and Sterility, vol. 66, No. 3, Sep. 1996: pp. 430–434.

Internet Search Results, National Library of Medicine, Search Topics: *Vitamin B12 and oligospermia: Zinc sulphate and infertility: zinc and sperm count: Folate and human fertility,* www.ncbi.nlm.nih.gov/entrez, Mar. 29, 2000–Apr. 5, 2000, 7 pages.

Amezuca et al.; *Nitric Oxide synthesized from L–Arginine regulates vascular tone in the coronary circulation of the Rabbit;* Brit. Journal of Pharmacology; Aug. 1989: 97(4); 1119–24 (Abstract only).

Andrews et al.; *Low–density Lipoproteins inhibit Endothelium–dependent Relaxation in Rabbit Aorta;* Nature, May 1987; 327:237–39.

Barbul et al.; *Arginine Stimulates Lymphocyte Immune Response in Healthy Human Beings;* Aug. 1981; Surgery 90(2); 244–51.

Barbul; *Arginine: Biochemistry, Physiology, and Therapeutic Implications;* JPEN; Mar./Apr. 1986; 10(2); 227–38.

Bath et al.; *Nitric Oxide and Prostacyclin: Divergence of Inhibitory Effects of Monocyte Chemotaxis and and Adhesion to Endothelium in Vitro;* Arteriosclerosis and Thrombosis, 1991; 11(2), 254–60.

Berdeaux, A.; *Nitric Oxide: An Ubiquitous Messenger;* Fundamental Clinical Pharmacology; 1993; 7:401–11.

Bornhof; *Hemodynamic Splanchnic and Renal Changes Associated with Administration of Arginine–hydrochloride in Dogs;* Res. Exp. Med.; 1980; 177:57–70.

Calver et al.; *Dilator Actions of Arginine in Human Peripheral Vasculature;* Clinical Sciences, Nov. 1991; 81;695–700.

Chen & Sanders; *L–Arginine Abrogates Salt–sensitive Hypertension in Dahl/Rapp Rats;* Journal of Clinical Investigations, Nov. 1991; 88: 1559–67.

Chua et al.; *Detection of Interluminal Release of Endothelium–derived Relaxing Factor from Human Saphenous Veins;* Circulation; Nov. 1993; 88(5); 128–32.

Cooke; *Endothelial Dysfunction in Disease States;* Current Opinion in Cardiology; 1990; 5:637–44.

Cooke et al.; *Arginine Restores Cholinergic Relaxation of Hypercholesterolemic Rabbit Thoracic Aorta;* Circulation, Mar. 1991; 83(3): 1057–62.

Cooke; *Endothelium–derived Factors and Peripheral Vascular Disease;* Cardiovascular Clin.; 1992; 22(3); 3–17.

Cooke et al.; *Antiartherogenic Effects of L–Arginine in the Hypercholesterolemic Rabbit;* Journal of Clinical Investigations; Sep. 1992; 90:1168–72.

Creager et al.; *L–Arginine Improves Endothelium–dependent Vasodilation in Hypercholesterolemic Humans;* Journal of Clinical Investigations; Oct. 1992; 90:1247–52.

Daly et al.; *Immune and Metabolic Effects of Arginine in the Surgical Patient;* Ann. Surg.; Oct. 1988; 208(4); 512–23.

Drexler et al.; *Correction of Endothelial Dysfunction of Hypercholesterolaemic Patients by L–Arginine;* The Lancet, vol. 338, 1546–50.

Fineman et al.; *L–Arginine, a Precursor of EDFR in Vitro, Produces Pulmonary Vasodilation in Lambs;* Am. Journal of Physiology; Nov. 1991; 261(5); 1563–69.

Furchgott & Zawadzki; *The Obligatory Role of Endothelial Cells in the Relaxation of Arterial Smooth Muscle by Acetylcholine;* Nature; Nov. 1980; 288:373–76.

Garg and Hassid; *Nitric oxide generating Vasodilators and 8–bromo–cyclic Guanosine Monophophate Inhibit Mitogenesis and Proliferation of Cultured Rat Vascular Smooth Muscle Cells;* Journal of Clinical Investigation, May 1989; 83:1774–77.

Girerd et al.; *L–Arginine Augments Endothelium–dependent Vasodilation in Cholesterol–fed Rabbits;* Circulation Research, 1990; 67(6), 1301–08.

Harrison et al.; *Normal and Pathophysiological Considerations of Endothelial Regulation of Vascular Tone and their Relevance ti Nitrate Therapy;* Am. Journal of Cardiology; Sep. 1992; 70:11B–17B.

Heistad et al.; *Augmented Responses to Vascoconstrictoe Stimuli in Hypercholesterolemic and Arthurosclerotic Monkeys;* Circulation Research, 1984; 54(6), 711–18.

Ignarro; *Endothelium–derived Nitric Oxide: Actions and Properties;* FASEB Journal; Jan. 1989; 3(1); 31–6; (Abstract only).

Ignarro et al.; *Basic Polyamino Acids Rich in L–Arginine . . . ;* Circulation Research, Feb. 1989; 64(2), 315–29.

Imaizumi et al; *Effects of L–Arginine on Forearm Vessels and Responses to Acetylcholine;* Hypertension; Oct. 1992; 20(4): 511–17.

Jeserich et al.; *Reduced Plasma L–Arginine in Hypocholesterolaemia;* The Lancet, Feb. 1992 (339:561).

Kanno et al.; *L–Arginine Infusion Induces Hypotension and Diuresis/Natriuresis with Concominant Increased Uriary Excretion of Nitrite/Nitrate and Cyclic GMP in Humans;* Clin. Exper. Pharmacol. Physiol.; Sep. 1992; 19:619–25.

Katan et al.; *Reduction of Casein–induced Hypercholesterolaemia and Artherosclerosis in Rabbits and Rats by Dietary Glycine, Arginine, and Alanine :* Artherosclerosis; Jun. 1982; 43:381–91.

Korbut et al.; *Effect of L–Arginine on Plasminogen Activator Inhibitorin Hypertensive Patients with Hypercholesterolemia ;* The New England Journal of Medicine, Jan. 1993; 328(4): 287–288.

Kubes et al.; *Nitric Oxide: An Endogenous Modulator of Leukocyte Adhesion;* Proceedings of the Nat. Acad. of Science, USA, Jun. 1991; 88:4651–55.

Kugiyama et al.; *Impairment of Endothelium–dependent Arterial Relaxation by Lysolecithin in Modified Low–density Lipoproteins;* Nature, 1990; 344:160–62.

Kuo et al.; *Pathophysiological Consequences of Arteroscle-rosis extend into the CoronaryMicrocirculation;* Circulation Research, 1992; 70(3), 465–76.

Lankin; *Artherosclerosis as a Free Radical Pathology;* International Congress Series 998,(Oxygen Radicals, Proceedings of the 5th International Congress on Oxygen Radicals, Kyoto, Japan;Nov. 17–21, 1991); 1992; pp. 385–388.

McNamara et al.; *L–Arginine Inhibits Ballooon Catheter . . . ;* Biochemical/Biophysical Research Communications, May 1993; 193(1), 291–96.

Meredith et al.; *Role of Endothelium in Ischemic Coronary Syndromes;* American Journal of Cardiology; Sep. 1993; 72:27C–32C.

Minor et al.; *Diet–induced Arteriosclerosis Increases the Release of Nitrogen Oxides from Rabbit Aorta;* Journal of Clinical Investigations, 1990; 86:2109–16.

Mitchell et al.; *Native LDL Inhibits the Release of Endothelil Derived Relaxing Factor by Reducing he Activity of Endothelial Nitric Oxide Synthase;* Journal of Vascular Research, 1992; 29:169.

Mollace et al.; *Evidence that Pharmacological Manipulations of central L–Arginine–NO Pathway influence Blood Pressure and Heart Rate in Rats;* Neurosci. Lett.; Mar. 1992; 137(1); 87–90 (Abstract only).

Murakami et al.; *Effects of L–Arginine on Systemic and Renal Haemodynamics in Conscious Dogs;* Clinical Science; Dec. 1991; 81:727–32.

Nakaki et al.; *L–Arginine Induced Hypertension;* The Lancet, Sep. 1990; 336:696.

Pearson, D. & Shaw, S.; *Life Extension: A Practical Scientific Approach;* Warner Books: Inc., 75 Rockefeller Plaza, New York, NY 10019; Jun. 1982 (Selected pages).

Pique et al.; *The Vasodilator Role of Endogenous Nitric Oxide in the Rat Gastric Microcirculation;* European Journal of Pharmacology; Dec. 1989; 174:293–96.

Pohl & Busse; *EDRF Increases Cyclic GMP in Platelets during Passage through the Coronary Vascular Bed;* Circulation Research, 1989; 65(6), 1798–1803.

Radomski et al.; *Comparative Phamocology of Endothelium–derived Relaxing Factor, Nitric Oxide and Prostacyclin in Platelets;* Brit. Journal of Pharmacology, 1987; 92:181–87.

Rees et al.: *Role of Endothelium–derived Nitric Oxide in the Regulation of Blood Pressure;* Proc. of Nat. Acad Science; May 1989; 3375–78.

Rocic et al.; *L–Arginyl, L–Lysine and L–Argynal/L–Arginine . . . ;* Medical Science Research, 1990; 18:165–66.

Ross; *The Pathogenesis of Arteriosclerosis—an Update;* New England Journal of Medicine, 1986; 314(8), 488–500.

Rossitch, Jr. et al.; *L–Arginine Normalizes Endothelial Function in Cerebral Vassels of Hypercholesterolemic Rabbits;* Journal of Clinical Investigations, Apr. 1991; 87:1295–99.

Rubyani: *Reversal of Hypercholesterolaemic–induced Endothelial dysfunction by L–Arginine;* Circulation; Mar. 1991; 83(3); 1118–20.

Saito et al.; *Metabolic and Immune Effects of Dietary Arginine Supplementation after Burn;* Arch. Surg.; Jul. 1987; 12:784–89.

Schini & Vanhoutte; *Nitric Oxide and and Vascular Smooth Muscle Homeostasis;* Arch. Mal Coeur; Nov. 1993; 86(1); 83–89 (Article in French) (Summary (on last page) in English).

Stamler et al.; *N–Acetylcysteine Potentiates Platelet Inhibition by Endothelium–derived Relaxing Factor;* Circulation Research, 1989; 65(3); 789–95.

Tanner et al.; *Oxidized Low Density Lipoproteins Inhibit Relaxations of Porcine coronary Arteries;* Circulation, Jun. 1991; 83(6); 2109–16.

Tomita et al.; *Rapid and Reversible Inhibition by Low–density Lipoprotein of the endothelium–dependent Relaxation to Hemostatic Substances;* Circulation Research, Jan. 1990; 66(1), 18–27.

Vallance et al.; *Effects of Endothelium–derived Nitric Oxide on Peripheral Arteriolar Tone in Man;* The Lancet, Dec. 1990; 336(8730): 1589–90 (Abstract only).

Vane & Botting; *The Role of Chemical Mediators Released by the Endothelium in the Control of the Cardiovascular System;* International Journal of Tiss. Reac.; 1992; 24(2); 55–64.

Visek ; *Arginine Needs, Physiological State, and Usual Dies; A Reevaluation;* Journal of Nutrition; Jan. 1986; 116:36–46.

Weidinger et al.; *Persistent Dysfunction of Regenerated Endothelium after balloon angioplasty of Rabbit Iliac Artery;* Circulation, 1990; 81(5), 1667–79.

Whitaker, J.: *Health and Healing* vol. 4(11) (Nov. 1994).

Whitaker, J.: *Health and Healing* vol. 5(9) (Sep. 1995).

Williams, D.; *Another vanishing cure?;* Alternatives for the Health Conscious Individual; vol. 5(17); (Nov. 1994).

Yamamoto et al.; *Videomicroscopic Demonstration of Defective Cholinergic Arteriolar Vasodilation in Artheriosclerotic Rabbit;* Journal of Clinical Investigation, 1988; 81:1752–58.

Zembowicz, A.; *The Biological Role of L–Arginine/Nitric Oxide Pathway;* Folia Med. Cracov., 1992; 33:103–16 (In Polish).

Agostoni et al.; *L–Arginine therapy in Reynaud's phenomenon?;* Inter. J. Clin. Lab. Research; 1991; 21: 202–3.

Aisaka et al.; *L–Arginine Availability Determines the Duration of Acetycholine–induced Systemic Vasodilation in Vivo;* Biochemical and Biophysical Research Communications; Sep. 1989; 163(2):710–17.

Albina et al.; *Regulation of Macrophage Functions by L–Arginine;* Journal of Experimental Medicine; Mar. 1989; 169:1021–29.

Albina, J. E., & Mateo, R. B.; *Nitric Oxide;* Amino Acid Metabolism and Therapy in Health and Nutritional Disease, Chapter 7; 1995; CRC Press Inc.; pp. 99–115.

Barbul et al.; *High Arginine Levels in Intravenous Hyperalimentation Abrogate Post–traumatic Immune Suppression;* Journal of Surgical Research; 1984; 36: 620–24.

Barbul et al.; *Intravenous Hyperlimentation with High Arginine Levels Improves Wound Healing and Immune Function;* Journal of Surgical Research; 1985; 38: 328–34.

Barnes, R. J. & Elmslie, R. G.; *The Effect of Calcium Ions on the Hydrolysis of Benzoyarginine ethyl Ester by Porcine Enteropeptidase;* Biochemica et Biophysica Acta; 1976; 452: 161–64.

Beckel, R.W. & Waller, G. R.; *Antioxidative Arginine–xylose Maillard Reaction Products; Conditions for Synthesis:* Journal of Food Science; May–Jun. 1983; 48(3): 996–97.

Berson et al.; *A two–year trial of low protein, low arginine diets or vitamin B6 for patients with Gyrate Atrophy;* Birgh Defects: Original Article Series; 1982; 18(6): 209–18.

Blakeslee, Sandra; *Chemical a Factor in Male Impotence;* New York Times (National Edition); Jan. 9, 1992; pp. A1 and B10.

Boegehold, Matthew A.; *Reduced Influence of Nitric Oxide on Arteriolar Tone in Hyperrtensive Dahl Rats;* Hypertension; Mar. 1992; 19(3): 290–95.

Bokelman et al.; *Oral L–Arginine augments abnormal endothelium–dependent skeletal muscle vasodilation in patients with coronary artery disease;* Supp. to Circulation; Oct. 1995; 92(8): 1–19 (Abstract only).

Bradbury; *Nobel Prize for Medicine;* The Lancet; Oct. 22, 1988; p. 977.

Buchmiller–Rouiller et al.; *Macrophage activation for intracellular killing as induced by a Ca2+ ionophore;* Biochemical Journal; 1992; 284: 387–92.

Cachofeiro, V., & Nasjletti, A.; *Increased vascular responsiveness to bradykinin in kidneys of spontaneously hypertensive rats. Effects of N–Omega–nitro–L–arginine;* Hypertension; Nov. 1991; 18(5): 683–88 (Abstract only).

Campillo et al.; *Effect of various concentrations of calcium on arginine–induced insulin and glucagon release in vitro;* Revista Espanola de Fisiologia; Jun. 1978; 34(2): 191–98.

Caramelo et al.; *Interaction of arginine vasopressin and angiotensin II on Ca2+ in vascular smooth muscle cells;* Kidney International; 1990; 38: 47–54.

Chen, P. Y., & Sanders, P. W.; *L–arginine abrogates salt–sensitive hypertension in Dahl/Rapp rats;* J Clin Invest; Nov. 1991; 88(5) 1559–67 (Abstract only).

Chiueh, C. C.; *Neurobiology of NO and OH: Basic Research and Clinical Relevance;* The Neurobiology of NO & OH; Annals of the NY Acad. of Sciences; 1994; 738: 279–81.

Cooke et al.; *Endothelial Dysfunction in Hypercholesterolemia is Corrected by L–Arginine;* Basic Res. in Cardiology; 1991; 86:173–81.

Cooke & Tsao; *Cellular Mechanisms of Artherogenesis and the Effects of Nitric Oxide;* Current Opinions in Cardiology; Oct. 1992; 7:799–804.

Devril et al.; *Arinine Modification in Elastase;* Journal of Biological Chemistry; 1984; 259(6):3851–57.

DiPolo & Beauge; *Phosphoarginine stimulation of $Na^+$—$Ca^{2+}$ exchange in squid axons;* Journal of Physiology; 1995; 487.1: 57–66.

DiRosa, M.; *Azione Antiammoniemica . . . (in Italian);* Cl. Terap.; Sep. 30, 1967; 42(6): 499–507.

Dohi et al.; *Activation of Endothelial L–Arginine Pathway in Resistance Arteries;* Hypertension; Aug. 1990; 16(2): 170–79.

DuBois–Rande et al.; *Effects of Infusion of L–Arginine into the Left Anterior Descending Coronary Artery . . . ;* American Journal of Cardiology; Nov. 15, 1992; 70: 1269–75.

Efron et al.; *Nitric Oxide generation from L–Arginine is required for optimal human peripheral blood lymphocyte DNA synthesis;* Surgery; Aug. 1991; 110(2): 327–34.

Elferink & Deierkauf; *Permeabilization and Calcium–dependent activation of Rabbit polymorphonuclear leucocytes by Poly–L–Arginine;* Inflammation; Apr. 1989; 13(3): 285–94.

Fleming et al.; *Effects of a phorbal ester and diacyglycerols on secretion of mucin and arginine esterase by rat submandibular gland calls;* Pflugers Archive, European Journal of Physiology; Jan. 1986; 406(1): 6–11.

Fujihara et al.; *Arginine Vasopressin Increases Perinuclear ($Ca^{2+}$)in Single Cultured Vascular Smooth Muscle Cells of Rat Aorta;* Journal of Vascular Research; Jul–Aug. 1993; 30.4.93: 231–38.

Fujihara, Hideyoshi; *Effects of Halothane on the Arginine–vasopressin–inducedSpatial . . . ;* Journal of theNiigata (Japan) Medical Society; 1993; 107(8): 728–37 (Article in Japanese, Abstract in English).

Gilligan et al.; *Contribution of Endothelium–derived Nitric Oxide to Exersise–induced Vasodilation;* Circulation; Dec. 1994; 90(6): 2853–58.

Girerd et al.; *L–Arginine Augments Endothelium–dependent Vasodilation in Cholesterol–fed Rats;* Circulation Research; Dec. 1990; 67(6): 1301–08.

Gold et al.; *Depletion of arterial L–Arginine causes reversible tolerance to endothelium–dependent relaxation;* Biochemical and Research Communications; Oct. 31, 1989; 164(2): 714–21.

Gold, M.; *The effects of calcium, magnesium, and L–Arginine on biosynthesis of . . . ;* Dissertation Abstracts International; Apr. 1991; 51(10): 4793B.

Gulati et al.; *Functional Role of Arginine–11 in the N–trminal Helix of . . . ;* Biochemistry; 1995; 34(22): 7348–55.

Harnon et al.; *Long–term Oral Administration of L–Arginine Reduces Intimal Thickening and . . . ;* Circulation; Sep. 1994; 90(3): 1357–62.

Hatton et al.; *Arginine vasopressin mobilises intracellular calcium via $V_1$receptor activation . . . ;* Brain Research; 1992; 588: 75–83.

Hecker et al.; *Mechanisms of shear stress–dependent endothelial nitric oxide release: cardiovascular implications;*in "Biochemical, Pharmacological, and Clinical Aspects of Nitric Oxide" Plenum Press, New York, NY, 1995; 49–54.

Hendler, S. S.; *The Doctor's Vitamin and Mineral Encyclopedia;* Simon & Schuster, New York, NY; 1990; (Selected pages).

Henrikson et al.; *Separation and identificationof two components of an estrogen–responsive , calcium–dependent arginine esteropeptidase;* Journal of Steroid Biochmistry; 1987; 26(2): 186–96.

Herchuelz et al.; *Mechanism of arginine–stimulated $Ca^{2+}$ influx into pancreatic B cell;* American Journal of Physiology; Jan. 1984; 246(1):E38–E43.

Hirooka et al,; *Effects of L–Arginine on Imparied Acetylcholine–induced and Ischemic Vasodilation of the Forearm in Patients with Heart Failure;* Circulation; Aug. 1994; 90(2): 658–68.

Hirooka et al.; *Effect of L–Arginine on Acetylcholine–induced endothelium–dependent vasodilation differs between . . . ;* Journal of the American College of Cardiology; Oct. 1994; 24(4): 948–55.

Hishikawa et al.; *L–Arginine as an antihypertensive agent;* Journal of Cardiovascular Pharmacology; 1992; 20 Supp. 12: S196–97 (Abstract only).

Hishikawa et al.; *Role of L–Arginine–Nitric Oxide Pathway in Hypertension;* Journal of Hypertension; Jun. 1193; 11(6):639–45.

Hogan et al.; *A Cysteine–for–Arginine Substitution (R614C) in the Human Skeletal Muscle Calcium Releasre Channel Cosegregates with Malignant Hyperthermia;* Anesth. Anal.; 1992; 75:441–48.

Hosang, Markus; *Suramin Binds to Platelet–derived Growth Factor and Inhibits Its Biological Activity;* Journal of Cellular Biochemistry; 1985; 29(3): 265–73.

Ishikawa et al.; *Arginine Vasopressin Increases Cellulat Free Calcium Concentration and . . . ;* Endocrinology; 1988; 123(3); 1376–84.

Ishikawa & Saito; *Effect of ouabain on cellular free calcium and cellular cyclic AMP production in response to arginine vasopressin . . . ;* Journal of Endocrinology; Jun. 1989; 121(3): 467–77.

Jacobs et al.; *Inhibition of endothelium–derived nitric oxide and artherosclerosis;* Ch. 14 in "Nitric oxide from L–Arginine: a bioregulatory system"; 1990; Elsevier Science Publishers; 107–114.

Janssens, P.A. et al.; *Calcium–independent stimulation of glycogenolysis by arginine vasotocin and catecholamines in liver of the axolotl;* Journal of Endocrinology; Apr. 1986; 109(1): 75–84.

Janssens, S.P. et al.; *Cloning and Expression of a cDNA encoding Human Endothelium–derived Relaxing Factor/Nitric Oxide Synthase;* The Journal of Biological Chemistry; Jul. 25, 1992; 267(21): 14519–522.

Johansson et al.; *The actions of arginine and glucose on glucagon secretion are mediated by opposite effects on cytoplasmic $Ca^{2+}$;* Biochemical and biophysical research communications; Aug. 31, 1987; 147(1): 309–14.

Kadirvel & Kratzer; *Uptake of L–Arginine and L–Lysine by the Small Intestine and Its Influence on Arginine–Lysine Antagonism in Chicks;* The Journal of Nutrition; Mar. 1974; 104(3): 339–43.

Keck et al.; *Influence Exercised by Elevated Serum Calcium Levels on the Arginine Infusion andInsulin Tolerance Test;* akt. endocrin.; Apr. 1980; 1(2): 135–42 (Article in German, Abstract in English).

Keysary et al.; *The Involvement of L–Arginine–Nitric Oxide Pathway in the Anti–rickettsial Activity of Macrophagelike Cells;* in "Biochemical, Pharmacological, and Clinical Aspects of Nitric Oxide" Plenum Press, New York; 1995; 111–14.

Kim et al.; *A Nitric Oxide–like Factor Mediates Nonadrenergic–Noncholinergic Neurogenic Relaxation of Penile Corpus Cavernosum Smooth Muscle;* Journal of Clinical Investigation; Jul. 1991; 88:112–18.

Kobayashi et al.; *Comparison of vasopressor effects of nitro arginine in stroke–prone spontaneously hypertensive rats and Wistar–Kyoto rats;* Clinical Experiments in Pharmacological Physiology; Sep. 1991; 18(8): 599–604 (Abstract only).

Koshland, D.E. Jr.; *Editorial (and supporting article)* : *The Molecule of the Year;* Science: Dec. 18, 1992; 258: 1861–65.

Leclercq–Meyer et al.; *The Role of Calcium in Glucagon Release;* Hormone Research; 1976; 7(6): 348–62.

Lefer et al; *Role of Endothelium–derived Relaxing Factor as a Cardio–protective Agent in Myocardial Ischemica;* in "Endothelium–Derived Contracting Factors"; Basel, Switzerland; Karger, 1990; pp. 190–97.

Levenson & Seifter; *Influence of Supplemental Arginine and Vitamin A on Wound Healing, the Thymus and Resistance to Infection following Injury;* Ch.5 in "Nutritional Support of the Seriously Ill Patient" Academic Press, New York; 1983; 53–62.

Levi et al.; *Evidence that L–Arginine is the biosynthetic presursor of vascular and cardiac nitric oxide;* Ch. 4 in "Nitric Oxide from L–Arginine: A Bioregulatory System"; Elsevier science Publishers, B.V.; 1990 35–44.

Lopez–Farre et al.; *Inhibition of L–Arginine of the endothelin–mediated increase in cytosolic calcium in human neutrophils;* Biochemical and Biophysical Research Communication; Aug. 15, 1991; 178(3): 884–891.

Lugg et al.; *The Role of Nitric Oxide in Erectile Function;* Journal of Andrology; Jan./Feb. 1995; 16(1): 2–4.

Luscher & Bock; *The endothelial L–Arginine/nitric oxide pathway and the renal circulation;* Klinische Wochenshrift; Sep. 3, 1991; 69(13): 603–09 (Abstract in English only).

Marin & Sanchez–Ferrer; *Role of endothelium–formed nitric oxide on vascular responses;* General Pharmaoclogy; 1990; 21(5): 575–87 (Abstract only).

Martasek et al.; *Hemin and L–Arginine regulation of blood pressure in spontaneous hypertensive rats;* Journal of American Social Nephrology; Dec. 1991; 2(6): 1078–84 (Abstract only).

Mayer & Bohme; $Ca^{2+}$–*dependent formation of an L–Arginine–derived activator of solubleguanylyl cyclase in bovine lung;* FEBS Letters; Oct. 1989; 256(1.2): 211–14.

Merimee et al.; *Arginine infusion in maturity–onset diabetes mellitus;* The Lancet (Preliminary Communications); Jun. 11, 1966; 1300–01.

Meyer–Lehnert et al.; *Atrial Natriuretic Factor (ANF) Inhibits Arginine Vasopressin–stimulated $Ca^{2+}$ Fluxes and Cell Contraction in Vascular Smooth Muscle Cells;* Klinische Wochenshrift; 1987; 65(Supp VIII): 115–21.

Miller et al.; *Determinants of Platelet Intercelluler Free Calcium in Essential Hypertension and Effect of Stimulation by Arginine Vasopressin;* American Journal of Hypertension; Mar. 1993; 6(3–1): 209–16.

Milyutina et al.; *Antiradical and antioxidative effect of arginine and its influence on lipid peroxidation activity during hypoxia;* Russian Bulletin of Experimental Biology and Medicine; Sep. 1990; 110(9): 1198–1200 (Translated from Russian).

Moncada, S.; *Introduction;* Ch. 1, from "Nitric Oxide from L–Arginine: A bioregulatory System"; Elsevier Science Publishers, B. V.; 1990; 1–3.

Moncada et al.; *Biosynthesis of nitric oxide from L–Arginine* Biochemical Pharmacology; Jun. 1, 1989; 38(11): 1709–15.

Moncada & Higgs; *The L–Arginine–nitric oxide Pathway;* The New England Journal of Medicine; Dec. 30, 1993; 329(27): 2002–12.

Moro et al.; *Activation of adrenal medullary L–arginine: nitic oxide pathway by stimuli which induce the release of catecholamines:* European Journal of Pharmacology—Molecular Pharmacology Section; Aug. 15, 1993; 246(3): 213–18.

Mulsch et al.; *Cytosolic nitric oxide synthesis from L–arginine in mammalina cells;* Progress in Pharmacology and Clinical Pharmacology 1991; 8(3): 73–82.

Nakaki et al.; *L–arginine–induced hypotension* ; The Lancet; Sep. 15, 1990; 336(8716): 696 (Letter: Abstract and text not available).

Nakaki & Kato; *Beneficial Circulatory Effect of L–Arginine;* Japanese Journal of Pharmacology; 1994; 66: 167–71.

Naruse, Masahiro; *Arginine vasopressin increases intracellular calcium ion concentration in isolated mouse collecting tubule cells: . . . ;* Japanese Journal of Nephrology; Mar. 1992; 34(4): 337–47.

Nunokawa et al.; *Cloning of inducible nitric oxide synthase in rat vascular smooth muscle cells;* Biochemical and Biophysical Communications; Feb. 26, 1993; 191(1):89–94.

Olson & Hertelendy; *Avian shell gland contractility: interaction od $PGF_{2+}$and arginine vasotocin with $Ca^{2+}$;* American Journal of Physiology; Mar. 1983; 244(3): C150–C157.

Palmer et al.; *Vascular endothelial cells synthesize nitric oxide from L–arginine;* Nature; Jun. 16, 1988; 333(6174): 664–66.

Palmer et al.; *L–Arginine is the physiological precursor for the formation of nitric oxide in endothelian–dependent relaxation;* Biochemical and Biophysical research Communications; Jun. 30, 1988; 153(3): 1251–56.

Panza et al.; *Effect of Increased Availability ofEndothelium–derived Nitric Oxide Precursor on . . . ;* Circulation; May 1993; 87(5): 1475–81.

Park et al.; *stimulation of lymphocyte natural cytotoxicity by L–arginine;* The Lancet; Mar. 16, 1991; 337: 645–46.

Qi et al.; *Evidence of L–Arginine/nitric oxide pathwy in endothelium and smooth muscle ofhuman internal mammary artery;* Biochemical and Biophysical research Communications; Aug. 31, 1993; 195(1): 90–96.

Rajifer et al.; *Nitric oxide as a mediator of relaxation of the corpus cavernosum in response to nonadrenergic, noncholinergic neurotransmission;* The New England Journal of Medicine; Jan. 9, 1992; 326(2):90–94.

Raju, T.N.K.; *Letter re Nobel Chronicles;* The Lancet: Jul. 29, 2000; 356: 436.

Rask et al.; *Studies on two physiological forms of the human retinol–binding protein differing in vitamin A and Arginine content;* Journal of Biological Chemistry; Nov. 10, 1971; 246(21): 6638–46.

Ribeiro et al.; *Pirrolidoncarbossilato di arginina e lisina nell'anziano;* Acta Gerontilogica; 1986; 36(1.2):69–76 (In Portuguese).

Saavedra–Molina & Pina; *Stimulation of L–ornithine uptake and L–citrulline and urea biosynthesis by D–arginine;* Biochemistry International; May 1991; 24(2): 349–57.

Schroder et al.; *L–Arginine potentiates and $N^G$ –monomethyl–L–arginine inhibits calcium ionophore–induced cyclic GMP stimulation in porcine aortic endothelial cells;* Ch. 6 in "Nitric Oxide from L–Arginine: A Bioregulatory System"; Elsevier Science Publishers, Amsterdam; 1990; 55–59.

Singh, H.J.; *The Effect of Intravenous Infusion of L–Arginine, Glycine and D–Lycine on Urinary Calcium Excretion in the Rat;* Japanese Journal of Physiology; 1995; 45(2): 327–36.

Sjostrand et al.; *The effects of L–Arginine and $N^G$–monomethyl L–Arginine on the inhibitory neurotransmission of the human corpus cavernosum penis;* Acta Physiol. Scand.; 1990; 140: 297–98.

Suton et al.; *Inhibition of voltage–activated $Ca^{2+}$ currents from cultured neurones by spermine, argiotoxin–636 and a synthetic polyamine;* Molecular Neuropharmaoclogy; Mar. 1993; 3(1): 37–43.

Tabrizchi & Triggle; *Actions of L– and D–Arginine and NG–monomethyl–L–Arginine on the blood pressure of pithed normotensive and spontaneously hypertensive rats;* Clin Exp Hypertension A; 1992; 14(3): 527–46 (Abstract only).

Takahara et al.; *Calcium–dependent Properties of Peptidlarginine Deiminase from Rabbit Skeletal Muscle;* Agricultural and Biological Chemistry; Nov. 1986; 50(11): 2899–2904.

Tanaka et al.; *Calcium–dependent Interactions with Calmodulin of a Fluorescent Calmodulin Antagonist: $N^2$–Dansyl–L–arginine–4–t–butylpiperidine Amide;* Archives of Biochemistry and Biophyisics; Jan. 1983; 220(1): 188–92.

Tsao et al.; *Enhanced Endothelial Adhesiveness in Hypercholesterolemia Is Attenuated by L–Arginine;* Circulation; May 1994; 89(5): 2176–82.

US Pharmacist Continuing Education; *The Role of L–Arginine in Cardiovascular Health;* ACPE Program No. 430–000–99–015–H01 (Lesson for Nov. 30, 2001).

Vallance et al.; *Endothelium–dependent responses and nitric acid . . . ;* Ch. 12; and Bult et al.; *Effects of chronic treatment with . . . ;* Ch. 13 in "Nitric Oxide from L–Arginine: a bioregulatory system" Elsevier Science Publishers, B.V.; 1990; 95–106.

Vallance et al.; *Accumulation of an endogenous inhibitor of nitric oxide synthesis in chronic renal failure;* The Lancet; Mar. 7, 1992; 339(8793): 572–75 (Abstract only).

Verrecchia et al.; *Nitric Oxide and Cerebral Ischemia;* Annals of the New York Academy of Sciences; pp. 341–345.

Wallace, Arthur; *Do Deficiencies of Endothelial Derived Relaxing Factor Contribute to Myocardial Stunning?;* Journal of Cardiac Surgery; Mar. 1993; 8(2)Supp.: 325–28.

Waller et al.; *Conditions for the Synthesis of Antioxidative Arginine–Xylose Maillard Reaction Products;* Ch. 8 in "The Maillard Reaction in Foods and Nutrition"; ACS Symposium Series #215, American Chemical Society, Washington, DC; 125–40.

Watanabe et al.; *Effects of vitamin E and Arginine on the metabolism of alcohol;* Nutrition Reports International; Jul. 1985; 32(1): 149–53.

Weil; *Natural Health, Natural Medicine—A Comprehensive Manual for Wellness and Self Care;* Houghton Mifflin Corp., Boston, MA; 1990; 226–27.

Wood & Allen; *Evidence for Insulin Involvement in Arginine– and Glucose–Induced Hypercalciuria in the Rat;* The Journal of Nutrition; Aug. 1983; 113(8): 1561–67.

Yen et al.; *Different Relaxation between L–Arginine and acetylcholine in spontaneously hypertensive rat aortae treated with NO omega–nitro–L–Arginine;* Chniese Journal of Physiology; 1991; 34(3): 257–66 (English Abstract only).

* cited by examiner

METHOD AND COMPOSITION FOR IMPROVING MALE FERTILITY HEALTH

This is a continuation-in-part of application Ser. 09/742,412 filed Dec. 22, 2000 now U.S. Pat. No. 6,497,885.

BACKGROUND OF THE INVENTION

Because of delayed child bearing, unhealthy diets and use of tobacco, caffeine, alcohol and drugs and environmental contaminants, difficulties in conceiving have been experienced.

Needs exist for pharmaceutical compounds that improve fertility in men.

SUMMARY OF THE INVENTION

This invention provides combinations of bioeffecting compounds for promoting fertility in men. The combinations include nutritional components that benefit fertility health. All the components have been studied separately, to determine their individual efficacy. The invention provides the first products to put these components together synergistically in men's formulations.

As many as 15% of couples in the U.S. have difficulty conceiving a child. In about one third of these cases, it is the man that is infertile; in another third, the female has fertility issues. The remaining is due to a combination of male and female fertility issues, or unknown causes. In many of these cases, causes of infertility are treatable. In almost 90% of the cases of low sperm count in men, the cause cannot be determined. Smoking and caffeine, drug and alcohol consumption, environmental toxicants, and stress are related to infertility in men. Reproductive organs are highly susceptible to free radical or oxidative damage from environmental toxicants and natural aging. A balanced, nutritional diet, and nutritional supplements with high antioxidant content can help reverse some of that damage. Other nutrients such as L-carnitine, B vitamins and zinc are critical to sperm formation and metabolism.

These and further and other objects and features of the invention are apparent in the disclosure, which includes the above and ongoing written specification with the claims.

DETAILED DESCRIPTION OF THE PREFERRED EMBODIMENTS

The invention provides combinations of beneficial bioeffecting compounds for promoting fertility in men. The invention provides a scientifically validated herbal/nutritional blend for men to improve fertility health by helping to improve sperm quality, count and motility. The combination of amino acids, herbs, vitamins and minerals improves overall health and helps with many of the deficiencies that decrease fertility.

The invention provides combinations of beneficial bioeffecting compounds for promoting fertility in men. Sperm are highly susceptible to free radical or oxidative damage from environmental toxicants and natural aging. Vitamins C and E, green tea, and selenium are all potent antioxidants that help improve sperm counts and quality. Ferulic acid, an antioxidant found in Dong quai, also improves sperm quality. Zinc and B vitamins (B6, B12 and folate) are critical nutrients in male reproductive systems for hormone metabolism, sperm formation and motility. The amino acid, L-carnitine, promotes formation of healthy sperm. L-carnitine fumarate is preferred. L-carnitine tartrate may be used.

The invention provides synergistic action of the combinations. Preferably, the distinct combinations are taken by both members of a couple in which the female age is between 21 and 46 (women's formula in patent application Ser. No. 09/742,412). The distinct combinations are useful for couples who have tried for 6 months or more, up to three years, to become pregnant without success. Preferably, patients take 2–4 capsules per day of the distinct formulas for three months.

Preferred ranges of the combinations considered in percent by weight are:

EXAMPLE 1

| Components | Minimum % | Maximum % |
|---|---|---|
| L-carnitine | 40 | 70 |
| Ferulic acid in Dong Quai | 0.1 | 10 |
| Vitamins C and E | 10 | 40 |
| Green tea | 1 | 20 |
| Selenium | 0.01 | 1 |
| Zinc | 0.1 | 10 |
| B Vitamins | 0.001 | 1 |

EXAMPLE 2

| Components | Minimum % | Maximum % |
|---|---|---|
| L-carnitine | 20 | 80 |
| Ferulic acid in Dong Quai | 0 | 20 |
| Vitamins C and E | .01 | 40 |
| Green tea | 0 | 30 |
| Selenium | 0 | 3 |
| Zinc | 0 | 15 |
| B vitamins | 0 | 5 |

An example of useful formulations in percent by weight is:

EXAMPLE 3

| Components | % Weight |
|---|---|
| L-carnitine | 50.4 |
| Dong quai (.190 ferulic acid) | 8 |
| Vitamins C and E | 23 |
| Green tea | 17 |
| Selenium | 0.1 |
| Zinc | 1.3 |
| B Vitamins | 0.2 |
| | 100% |

While the invention has been described with references to specific embodiments, modifications and variations of the invention may be construed without departing from the scope of the invention, which is defined in the following claims.

I claim:

1. A pharmaceutical composition for oral ingestion having fertility promoting activity in males comprising components present in the proportion in parts by weight of:
   about 5 to 50% green tea, vitamin C, vitamin E, and selenium,
   about 10 to 80% L-carnitine,
   up to about 1% ferulic acid in Dong quai,
   up to about 1% vitamins B6, B12, and folate,
   up to about 10% zinc.

2. The pharmaceutical composition of claim 1, wherein the components are present in the proportion in parts by weight of
- about 20 to 50% green tea, vitamin C, vitamin E, and selenium
- about 40 to 80% L-carnitine,
- about 0.01 to 1% feridic acid in Dong quai,
- about 0.003 to 1% vitamins B6 and B12, and folate
- about 1 to 10% zinc.

3. A pharmaceutical composition having fertility promoting activity in males comprising in combination components present in proportions in parts by weight of:
- about 5 to 50% green tea, vitamin C, vitamin E, and selenium,
- about 10 to 80% L-carnitine,
- about 0.01 to 1% ferulic acid in Dong quai,
- about 0.01 to 1% vitamins B6, B12, and folate,
- about 0.1 to 10% zinc.

4. A pharmaceutical composition for oral ingestion having fertility promoting activity in males comprising components present in the proportion in parts by weight of:
- about 20 to 80% L-carnitine fumarate,
- about 5 to 30% vitamins C and E,
- about 0.1 to 30% green tea,
- about 0.001 to 1% selenium,
- about 2 to 20% Dong quai,
- about 0.1 to 5% zinc, and
- about 0.001 to 1% vitamins B6, B12, and folate.

5. The pharmaceutical composition of claim 4 wherein the components are present in the proportion in parts by weight of
- about 20 to 80% L-carnitine fumarate,
- about 5 to 30% vitamins C and E,
- about 1 to 30% green tea,
- about 0.001 to 1% selenium,
- about 2 to 20% Dong quai,
- about 0.1 to 2% zinc, and
- about 0.001 to 1% vitamins B6, B12, and folate.

6. A pharmaceutical composition for oral ingestion having fertility promoting activity in males comprising in combination components present in the proportion in parts by weight of
- about 10 to 80% L-carnitine,
- about 5 to 50% vitamins C and E,
- about 1to 30% green tea,
- about 0.001 to 1% selenium,
- about 0.2 to 20% Dong quai,
- about 0.1 to 5% zinc, and
- about 0.001 to 1% vitamins B6, B12, and folate.

7. A pharmaceutical composition for oral ingestion having fertility promoting activity in males comprising in combination components present in the proportion in parts by weight of
- about 50% L-carnitine,
- about 23% vitamins C and E,
- about 8% Dong quai,
- about 1% selenium,
- about 2% zinc vitamins B6, B12, and folate, and
- about 16% green tea.

* * * * *